United States Patent
Tenerz

(10) Patent No.: US 7,931,671 B2
(45) Date of Patent: Apr. 26, 2011

(54) MEDICAL SEALING DEVICE

(75) Inventor: Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 389 days.

(21) Appl. No.: 11/077,361

(22) Filed: Mar. 11, 2005

(65) Prior Publication Data

US 2006/0206146 A1   Sep. 14, 2006

(51) Int. Cl.
*A61B 17/03* (2006.01)
(52) U.S. Cl. .......................................... 606/213; 606/151
(58) Field of Classification Search .................. 606/151, 606/157, 158, 213–217, 139, 153, 232, 200; 623/23.72; 604/57, 59, 60
See application file for complete search history.

(56) References Cited

U.S. PATENT DOCUMENTS

| 5,192,301 A | * | 3/1993 | Kamiya et al. ................. 606/213 |
| 5,342,393 A | | 8/1994 | Stack |
| 5,350,399 A | * | 9/1994 | Erlebacher et al. ............ 606/213 |
| 5,593,422 A | | 1/1997 | Muijs van de Moer et al. |
| 5,620,461 A | | 4/1997 | Muijs van de Moer et al. |
| 5,976,174 A | * | 11/1999 | Ruiz .............................. 606/213 |
| 6,160,084 A | | 12/2000 | Langer et al. |
| 6,281,262 B1 | * | 8/2001 | Shikinami ..................... 523/105 |
| 6,388,043 B1 | | 5/2002 | Langer et al. |
| 6,508,828 B1 | | 1/2003 | Akerfeldt et al. |

FOREIGN PATENT DOCUMENTS

WO   WO 2004/110315 A1   12/2004

* cited by examiner

*Primary Examiner* — Todd E Manahan
*Assistant Examiner* — Kathleen Sonnett
(74) *Attorney, Agent, or Firm* — Foley & Lardner LLP

(57) ABSTRACT

The invention relates to a medical sealing device (1) for the sealing of a puncture hole in a vessel wall, and comprises an inner member (2), which is adapted to be positioned at an interior surface of the vessel wall, and an outer member (3), which is adapted to be positioned outside the vessel wall, the inner member (2) and the outer member (3) being held together by a retaining member (4), wherein at least one of said inner member (2), outer member (3) and retaining member (4) is made from at least one shape memory polymer.

11 Claims, 2 Drawing Sheets

MEDICAL SEALING DEVICE

FIELD OF THE INVENTION

The present invention relates generally to the field of sealing devices for the sealing of a percutaneous puncture in a vessel wall, and in particular to the class of sealing devices that comprises an intra-arterial member and an extra-arterial member, which are sandwiching the vessel wall and are held together by a retaining member, and more particularly to a sealing device which at least partly is made from a polymer having a shape memory.

BACKGROUND OF THE INVENTION

In the U.S. Pat. No. 6,508,828, which is assigned to the present assignee, a sealing device is disclosed for sealing a puncture hole in a vessel wall. The sealing device comprises an inner sealing member, an outer member, and a retaining member. The inner sealing member is adapted to be positioned at the inner wall of a vessel, while the outer member is adapted to be positioned at the outer wall of the vessel. In use, the inner and outer members are sandwiching the vessel wall, and are held together by the retaining member to thereby seal the puncture hole in the vessel wall. The retaining member and the outer member are thereby held in place by friction acting between the retaining member and the outer member. The contents of U.S. Pat. No. 6,508,828 are hereby incorporated herein by reference.

Other examples of sealing devices that comprise an inner member and an outer member, which are held together by an elongated retaining member, such as a suture or filament, can be found in, for example, U.S. Pat. Nos. 5,593,422 and 5,620,461. In U.S. Pat. No. 5,342,393, the retaining member is in the form of a stem that extends from the inner member.

Although at least a sealing device designed according to the teachings of U.S. Pat. No. 6,508,828 in practice has proven to work very well, its sealing function can be improved, and in particular the friction locking between the retaining member and the outer member can be enhanced.

SUMMARY OF THE INVENTION

The general object of the present invention is therefore to provide a sealing device with an enhanced sealing capacity and which is more reliably positioned at a vessel wall. Preferably, the invention should be applicable to an existing sealing device with a minimum of change of the design of the components of the sealing device, and without changing the practical handling of the sealing device.

The above-mentioned objects are achieved with a sealing device as described below.

The present invention is related to a sealing device comprising an intra-arterial (inner) member and an extra-arterial (outer) member, which are held together by a retaining member. In use, the inner member is through a puncture hole in a vessel wall introduced into the lumen of the vessel, and is then retracted until it is in close contact with the inner vessel wall. The retaining member, which is attached to the inner member, then extends through the puncture hole and holds the inner member tightly in a fixed position. The outer member is then advanced along the retaining member until the outer member is contacting the outside of the vessel wall. When the operation is completed, the outer and inner members will thereby sandwich the vessel wall and the puncture hole therein, while the outer member and the retaining member are held together by friction locking.

According to the invention, the sealing performance of a sealing device, and in particular the locking function between a retaining member and an outer member can be improved by making the retaining member and/or the outer member from at least one polymer having a so-called shape memory. An object, i.e. the retaining member or the outer member, being made from such a polymer is characterized by having a first shape at a first temperature and a second shape at a second temperature.

In a first embodiment of the present invention, a retaining member, which is in the form of a stem extending from an inner member, is made from a polymer having shape memory. The stem would then have a first (smaller) diameter at a first temperature and a second (larger) diameter at a second temperature. A sealing device comprising this retaining member would be positioned at a vessel wall, with the stem being in the smaller diameter configuration, and the stem would then expand to its larger diameter configuration, to thereby provide a large amount of friction between the stem and an outer member which is positioned around the stem.

Rather than expand as a whole, the stem could also be provided with protrusions which at a first temperature are positioned close to the stem body, while at a second temperature are protruding away from the stem body to thereby prevent an outer member from sliding off the stem. This design is shown in a second embodiment of the invention.

In a third embodiment, the friction locking is provided by a spiral element which is disposed inside a retaining member in the form of a suture. The spiral element is made from a shape memory polymer, such that the spiral element has a first, small diameter during the introduction of a sealing device, of which the spiral element is a part, and a second, larger diameter when the sealing device has been positioned at a vessel.

Also an inner member could be made from a shape memory polymer. In a fourth embodiment of the present invention, the inner member and an outer member are made from a shape memory polymer such that the inner and outer members are essentially flat at a first temperature, and exhibit a concave shape at a second temperature. When the inner and outer members have been positioned such that they sandwich a vessel wall, the inner and outer members would then assume the concave shape, with their concave sides facing the vessel wall, to thereby squeeze the vessel wall between them.

DETAILED DESCRIPTION OF THE INVENTION

Figure 1A:
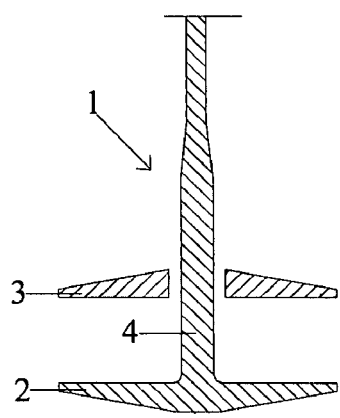
FIGS. 1a and 1b are schematic illustrations of a first embodiment of the present invention in a first state and in a second state.

A sealing device 1 according to the present invention is schematically illustrated in FIGS. 1a and b. The sealing device 1 comprises an inner member 2 and an outer member 3, which are held together by an elongated retaining member 4. The retaining member 4 protrudes from the inner member 2, and extends through a hole in the outer member 3. During the positioning operation of the sealing device 1, the inner member 2 is positioned at an inner wall of a vessel, and the outer member 3 is then slid along the retaining member 4 into abutment against an outer wall of the vessel. According to the invention, the retaining member 4 is made from at least one polymer having a shape memory.

Such a shape memory polymer, which is amorphous or at least partially amorphous, is characterized by its so-called glass transition temperature in that the polymer undergoes a transition from a pliable, elastic state at temperatures higher than the glass transition temperature to a brittle glass-like state at temperatures lower than the glass transition temperature. Here, it could be noted that such a transition of a polymer is not exactly related to its glass transition temperature; if, for example, a polymer being in its glass-like state for a long period of time is exposed to a temperature just below its glass transition temperature, the polymer will undergo a transition to a more elastic state. For the purpose of the present invention, shape memory polymers have a further interesting property. When a shape memory polymer is formed into a particular shape at a higher temperature, the polymer will "remember" this shape, such that when the polymer is cooled and forced into another shape, the polymer will assume its original shape upon heating to a temperature above the state transition temperature. Examples of shape memory polymers may, for example, be found in the U.S. Pat. Nos. 6,388,043 and 6,160,084. In the international application WO 2004/110315 is further described how an implantable stent, which comprises first and second layers of at least partially amorphous polymers, can assume a first shape at a first temperature and second shape at a second temperature. The contents of these three documents are incorporated herein by reference.

Figure 1B:
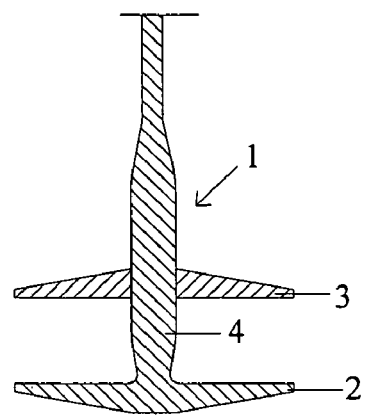

Returning now to FIGS. 1a and b, the retaining member 4, which is made from a shape memory polymer, was originally formed into the large diameter shape illustrated in FIG. 1b, and was then cooled and stretched to the smaller diameter configuration illustrated in FIG. 1a. When the sealing device 1, being at a temperature below the transition temperature, is positioned at a vessel wall, the outer member 3 can easily slide along the retaining member 4. When the sealing device 1, and in particular the retaining member 4, subsequently is warmed to a temperature which is above the glass transition temperature of the retaining member 4, the retaining member will return to its original shape, i.e. the large diameter configuration shown in FIG. 1b. In this state, the diameter of the retaining member 4 corresponds to the diameter of the hole in the outer member 3, which consequently is prevented from sliding along the retaining member 4. In FIG. 1a, the hole in the outer member 3 has been depicted as having a diameter that is considerably larger than the diameter of the retaining member 4. This is merely for illustrative purposes: in practice, the diameter of the retaining member 4 would initially only be insignificantly smaller than the diameter of the hole in the outer member 3. Correspondingly, without the presence of an outer member, a retaining member could expand to a diameter which is larger than the diameter of a hole in this outer member, to further increase the friction between the outer member and retaining member. It is also possible that the outer member 3 has been made from a shape memory polymer and formed in such a way that the hole in the outer member 3 contracts when the sealing device 1 is warmed to a temperature above the transition temperature. The transition temperature should be below the body temperature, i.e. below 37° C., and preferably well below the body temperature in order to have a fast transition from the state shown in FIG. 1a to the state shown in FIG. 1b. The latter is valid for all the embodiments of the present invention.

Figure 2A:
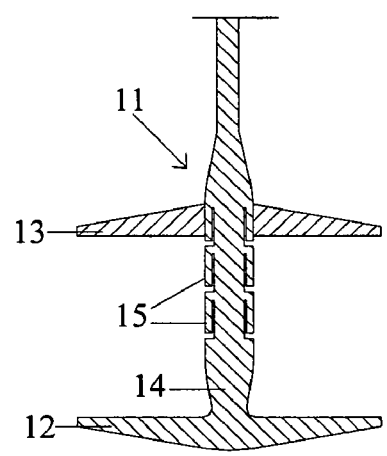
FIGS. 2a and 2b are schematic illustrations of a second embodiment of the present invention in a first state and in a second state.
Figure 2B:
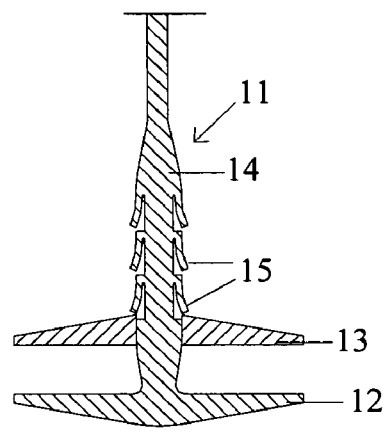

A second embodiment of a sealing device 11 according to the invention is illustrated in FIGS. 2a and b. Like the first embodiment described in conjunction with FIGS. 1a and b, the sealing device 11 comprises an inner member 12, an outer member 13, and a retaining member 14. Here, the retaining member 14 is further provided with protrusions 15 made from a shape memory polymer. These protrusions 15 were originally formed into the radially protruding configuration shown in FIG. 2b, and were then cooled and forced closer to the body of the retaining member 13, as is shown in FIG. 2a. When the sealing device 11, being at a temperature below the transition temperature, is positioned at a vessel wall, the outer member 14 can easily slide along the retaining member 14 and over the protrusions 15. When the sealing device 11, and in particular the protrusions 15, subsequently is warmed to a temperature which is above the glass transition temperature of the retaining member 14, the protrusions 15 will return to their original configuration, i.e. to the protruding configuration shown in FIG. 2b. In this configuration, the outer member 13 is effectively prevented from sliding along the retaining member 14.

Figure 3A:
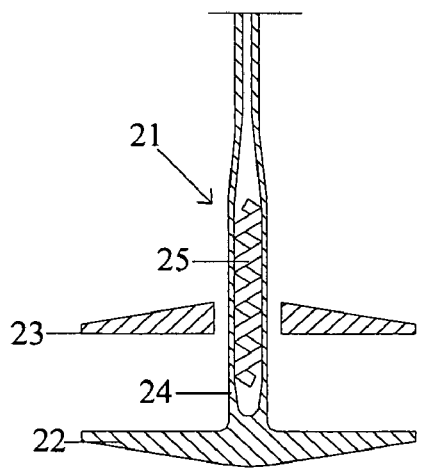
FIGS. 3a and 3b are schematic illustrations of a third embodiment of the present invention in a first state and in a second state.
Figure 3B:
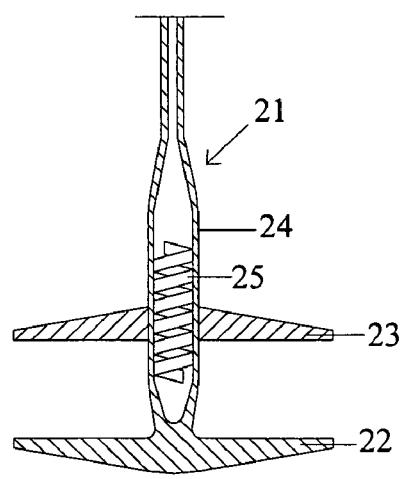

FIGS. 3a and b illustrate a third embodiment of the present invention. Here, a sealing device 21 comprises an inner member 22, an outer member 23, and an at least partly hollow retaining member 24, such as a suture, in the interior of which an expanding spiral element 25 has been placed. The spiral element 25, which is made from a shape memory polymer, was originally formed into the large diameter configuration shown in FIG. 3b, and was then cooled and compressed or stretched to the small diameter configuration shown in FIG. 3a. When the sealing device 21, being at a temperature below the transition temperature, is positioned at a vessel wall, the outer member 23 can easily slide along the retaining member 24. When the sealing device 21, and in particular the spiral element 25, subsequently is warmed to a temperature which is above the glass transition temperature of the spiral element 25, the spiral element will return to its original configuration, i.e. to the large diameter configuration shown in FIG. 3b. In this configuration the friction acting between the outer member 23 and the retaining member 24 prevents the outer member 23 from sliding along the retaining member 24.

Figure 4A:
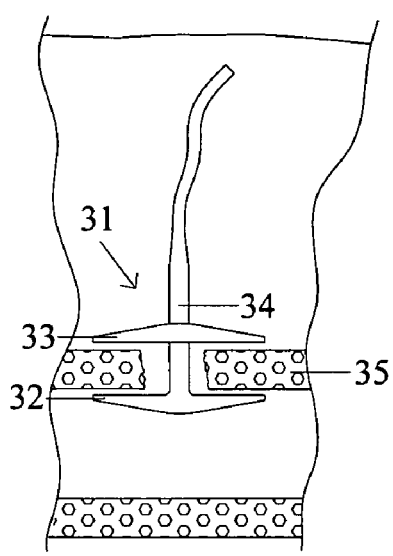
FIGS. 4a and 4b are schematic illustrations of a fourth embodiment of the present invention in a first state and second state.
Figure 4B:
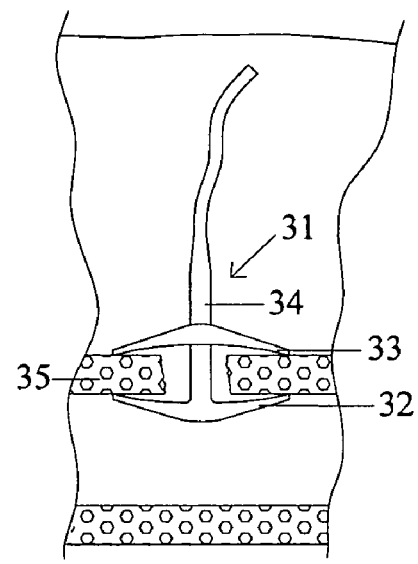

The previously described embodiments of a sealing device according to the invention were primarily directed to the locking function between an outer member and a retaining member. A reliable locking function is prerequisite for a reliable sealing function of a sealing device. In a fourth embodiment of the invention, which is depicted in FIGS. 4a and b, the memory properties of an inner member 32 and an outer member 33 are more directly directed to the sealing function of a sealing device 31. Besides the inner member 32 and outer member 33, the sealing device 31 comprises a retaining member 34. The inner member 32 as well as the outer member 33 are made from a shape memory polymer, and were originally formed into the bulging configuration shown in FIG. 4b. The inner and outer members 32, 33 were then cooled and flattened to the flat configuration shown in FIG. 4a. When the sealing device 31, being at a temperature below the transition temperature, is positioned at a vessel wall 35, the inner and outer members 32, 33 come to a position where their inner sides are essentially parallel with the vessel wall 35. When the sealing device 31, and in particular the inner and outer members 32, 33, subsequently is warmed to a temperature which is above the glass transition temperature of the inner and outer members 32, 33, the inner and outer members 32, 33 will return to their bulky configurations, i.e. to the configuration shown in FIG. 4b. In this configuration, the concave sides of the inner and outer members 32, 33 face the vessel wall 35; and due to the non-planar shapes of the inner and outer members, the vessel wall is tightly clamped between the inner and outer members 32, 33. In other words, the shape memory property of the polymer from which the inner and outer members 32, 33 are made provides an extra amount of clamping force, which thereby adds to the sealing capacity of the sealing device 31.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that the different shape memory parts of a sealing device according to the invention could be made from more than one shape memory polymer, which preferably is biodegradable (bioabsorbable), and the shape memory polymers could be provided as layers, as, for example, suggested in the above-referenced application WO 2004/110315. The invention is also applicable to the sealing of other types of holes or openings in the walls of bodily organs, such as atrial septal defects (ASD) or patent foramen oval (PFO).

What is claimed is:

1. A medical sealing device for sealing a hole in a wall of a body organ, comprising:
    an inner member adapted to be positioned against an interior surface of the wall;
    a retaining member attached to the inner member; and
    an outer member adapted to be positioned outside the wall, the outer member having a hole through which the retaining member passes;
    wherein the retaining member includes a hollow portion within the retaining member;
    wherein the retaining member comprises a shape memory polymer, wherein the shape memory polymer is located in the hollow portion such that the shape memory polymer is enclosed within the retaining member; and
    wherein in a first state, the outer member is slidably attached to the retaining member and in a second state, a cross-sectional dimension of the retaining member changes in comparison to the first state such that the outer member is fixedly attached to the retaining member due to a change in shape of the shape memory polymer;
    wherein the shape memory polymer is enclosed within the retaining member such that the shape memory polymer is located in the hollow portion while the medical sealing device is in the first state and before delivery of the medical sealing device to the hole in the wall of the body organ;
    wherein the shape memory polymer is positioned within the hollow portion of the retaining member such that at least a portion of the shape memory polymer is located within the hole of the outer member when the medical sealing device is in the second state.

2. A medical sealing device according to claim 1, wherein the retaining member has a first shape at a temperature below a transition temperature and a second shape above the transition temperature.

3. A medical sealing device according to claim 2, wherein the retaining member has a first diameter below the transition temperature and a second diameter above the transition temperature, and wherein the second diameter is larger than the first diameter.

4. A medical sealing device according to claim 2, wherein the outer member is provided with the hole, which has a first diameter below the transition temperature and a second diameter above the transition temperature, and wherein the second diameter is smaller than the first diameter.

5. A medical sealing device according to claim 2, wherein the inner member has a first side which is adapted to abut the interior surface of the wall of the body organ, and wherein the first side is essentially planar at a temperature below the transition temperature and is concave at a temperature above the transition temperature.

6. A medical sealing device according to claim 2, wherein the outer member has a first side which is adapted to abut an outer side of the wall of the body organ, and wherein the first side is essentially planar at a temperature below the transition temperature and is concave at a temperature above the transition temperature.

7. A medical sealing device according to claim 1, wherein the body organ is an artery, and wherein:
    the inner member is adapted to be positioned against an interior surface of the wall of the artery; and
    the outer member is adapted to be positioned outside the wall of the artery.

8. A medical sealing device according to claim 1, wherein the shape memory polymer is an expanding spiral element.

9. A medical sealing device according to claim 8, wherein a diameter of the expanding spiral element increases at a temperature above a transition temperature of the shape memory polymer.

10. A medical sealing device according to claim 1, wherein a diameter of the shape memory polymer increases at a temperature above a transition temperature of the shape memory polymer.

11. A medical sealing device according to claim 1, wherein the shape memory polymer is completely contained within the hollow portion.

* * * * *